(12) United States Patent
Tout et al.

(10) Patent No.: US 10,420,866 B2
(45) Date of Patent: *Sep. 24, 2019

(54) MANUALLY-ACTUATED, REDUCED-PRESSURE SYSTEMS FOR TREATING WOUNDS

(71) Applicant: KCI Licensing, Inc., San Antonio, TX (US)

(72) Inventors: Aidan Marcus Tout, Alderbury (GB); Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/711,832

(22) Filed: Sep. 21, 2017

(65) Prior Publication Data

US 2018/0008755 A1 Jan. 11, 2018

Related U.S. Application Data

(60) Continuation of application No. 14/145,723, filed on Dec. 31, 2013, now Pat. No. 9,795,722, which is a
(Continued)

(51) Int. Cl.
*A61M 1/00* (2006.01)
*A61M 27/00* (2006.01)
(Continued)

(52) U.S. Cl.
CPC ........ *A61M 1/0039* (2013.01); *A61M 1/0003* (2013.01); *A61M 1/0011* (2013.01);
(Continued)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Michele M Kidwell
*Assistant Examiner* — Ilya Y Treyger

(57) ABSTRACT

A manually-actuated, constant reduced-pressure apparatus for use with a reduced-pressure system for treating tissue at a tissue site includes a flexible, collapsible member that is operable to move between a compressed position and an extended position. The collapsible member may be disposed between a carrier member and a slider member that move between a compressed position and an extended position. The carrier member and slider member are urged away from each other by a constant-force biasing member, e.g., a constant force coil spring. As the apparatus moves from the compressed position to the extended position, a constant reduced-pressure is generated and delivered to a reduced-pressure port. Methods of manufacturing a manually-actu- (Continued)

ated, constant reduced-pressure apparatus and methods of treating a tissue site are also provided.

19 Claims, 6 Drawing Sheets

Related U.S. Application Data division of application No. 12/500,134, filed on Jul. 9, 2009, now Pat. No. 8,641,692.

(60) Provisional application No. 61/079,866, filed on Jul. 11, 2008.

(51) Int. Cl.
*A61F 13/00* (2006.01)
*A61F 13/02* (2006.01)
*A61B 17/50* (2006.01)

(52) U.S. Cl.
CPC ........ *A61M 1/0072* (2014.02); *A61M 1/0088* (2013.01); *A61M 27/00* (2013.01); *A61M 1/0009* (2013.01); *A61M 2205/071* (2013.01); *Y10T 29/49826* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,084,691 A | 4/1963 | Stoner |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,779,243 A | 12/1973 | Tussey et al. |
| 3,809,087 A | 5/1974 | Lewis, Jr. |
| 3,826,254 A | 7/1974 | Mellor |
| 3,875,941 A | 4/1975 | Adair |
| 4,080,970 A | 3/1978 | Miller |
| 4,096,853 A | 6/1978 | Weigand |
| 4,098,434 A | 7/1978 | Uhlig |
| 4,132,332 A | 1/1979 | Wassilieff |
| 4,139,004 A | 2/1979 | Gonzalez, Jr. |
| 4,141,361 A | 2/1979 | Snyder |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,278,089 A | 7/1981 | Huck et al. |
| 4,284,079 A | 8/1981 | Adair |
| 4,297,995 A | 11/1981 | Golub |
| 4,333,468 A | 6/1982 | Geist |
| 4,372,297 A | 2/1983 | Perlin |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,404,924 A | 9/1983 | Goldberg et al. |
| 4,419,097 A | 12/1983 | Rowland |
| 4,460,354 A | 7/1984 | Weilbacher et al. |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,578,060 A | 3/1986 | Huck et al. |
| 4,605,399 A | 8/1986 | Weston et al. |
| 4,608,041 A | 8/1986 | Nielsen |
| 4,640,688 A | 2/1987 | Hauser |
| 4,642,088 A | 2/1987 | Gunter |
| 4,643,719 A | 2/1987 | Garth et al. |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,798,583 A | 1/1989 | Beck et al. |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,903,726 A | 2/1990 | Martin et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,981,474 A | 1/1991 | Bopp et al. |
| 4,985,019 A | 1/1991 | Michelson |
| 5,019,059 A | 5/1991 | Goldberg et al. |
| 5,024,653 A | 6/1991 | Kohnke |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,102,404 A | 4/1992 | Goldberg et al. |
| 5,112,323 A | 5/1992 | Winkler et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,226,877 A | 7/1993 | Epstein |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki |
| 5,304,129 A | 4/1994 | Forgach |
| 5,318,548 A | 6/1994 | Filshie |
| 5,342,329 A | 8/1994 | Croquevielle |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carlon |
| 5,437,651 A | 8/1995 | Todd et al. |
| 5,527,293 A | 6/1996 | Zamierowski |
| 5,542,939 A | 8/1996 | Onodera et al. |
| 5,549,584 A | 8/1996 | Gross |
| 5,554,011 A | 9/1996 | Bales et al. |
| 5,556,375 A | 9/1996 | Ewall |
| 5,592,948 A | 1/1997 | Gatten |
| 5,607,388 A | 3/1997 | Ewall |
| 5,636,643 A | 6/1997 | Argenta et al. |
| 5,645,081 A | 7/1997 | Argenta et al. |
| 5,645,540 A | 7/1997 | Henniges et al. |
| 5,714,696 A | 2/1998 | Yeamans |
| 5,718,355 A | 2/1998 | Garby et al. |

(56) References Cited

U.S. PATENT DOCUMENTS

| | | |
|---|---|---|
| 5,819,990 A | 10/1998 | Cimentepe et al. |
| 5,827,246 A | 10/1998 | Bowen |
| 5,830,198 A | 11/1998 | Henniges et al. |
| 6,024,731 A | 2/2000 | Seddon et al. |
| 6,071,267 A | 6/2000 | Zamierowski |
| 6,135,116 A | 10/2000 | Vogel et al. |
| 6,174,306 B1 | 1/2001 | Fleischmann |
| 6,241,747 B1 | 6/2001 | Ruff |
| 6,261,276 B1 | 7/2001 | Reitsma |
| 6,287,316 B1 | 9/2001 | Agarwal et al. |
| 6,345,623 B1 | 2/2002 | Heaton et al. |
| 6,485,007 B1 | 11/2002 | Duelli |
| 6,488,643 B1 | 12/2002 | Tumey et al. |
| 6,493,568 B1 | 12/2002 | Bell et al. |
| 6,553,998 B2 | 4/2003 | Heaton et al. |
| 6,626,891 B2 | 9/2003 | Ohmstede |
| 6,648,862 B2 | 11/2003 | Watson |
| 6,656,149 B2 | 12/2003 | Ladd |
| 6,745,765 B2 | 6/2004 | Kullik et al. |
| 6,814,079 B2 | 11/2004 | Heaton et al. |
| 6,979,324 B2 | 12/2005 | Bybordi et al. |
| 7,004,915 B2 | 2/2006 | Boynton et al. |
| 7,070,584 B2 | 7/2006 | Johnson et al. |
| 7,625,362 B2 | 12/2009 | Boehringer et al. |
| 7,846,141 B2 | 12/2010 | Weston |
| 8,007,257 B2 | 8/2011 | Heaton et al. |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,267,083 B1 | 9/2012 | Goldstein et al. |
| 8,377,079 B2 | 2/2013 | Coe et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 8,961,481 B2 | 2/2015 | Hu et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0065494 A1 | 5/2002 | Lockwood et al. |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0198504 A1 | 12/2002 | Risk et al. |
| 2003/0040687 A1 | 2/2003 | Boynton et al. |
| 2004/0064132 A1 | 4/2004 | Boehringer et al. |
| 2004/0243105 A1 | 12/2004 | Swan et al. |
| 2005/0004534 A1 | 1/2005 | Lockwood et al. |
| 2005/0070858 A1 | 3/2005 | Lockwood et al. |
| 2005/0087556 A1 | 4/2005 | Signorini |
| 2005/0137539 A1 | 6/2005 | Biggie et al. |
| 2005/0197639 A1 | 9/2005 | Mombrinie |
| 2005/0261642 A1 | 11/2005 | Weston |
| 2005/0261643 A1 | 11/2005 | Bybordi et al. |
| 2006/0025727 A1 | 2/2006 | Boehringer et al. |
| 2006/0216171 A1 | 9/2006 | Hernandez |
| 2006/0229586 A1 | 10/2006 | Faries |
| 2007/0214692 A1 | 9/2007 | Ferrara |
| 2008/0183156 A1 | 7/2008 | Yoo |
| 2008/0306456 A1 | 12/2008 | Riesinger |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| CN | 2142728 Y | 9/1993 |
| CN | 1571682 A | 1/2005 |
| CN | 2745582 Y | 12/2005 |
| CN | 2829771 Y | 10/2006 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2006114648 A2 | 11/2006 |
| WO | 2007013064 A1 | 2/2007 |
| WO | 2007133618 A2 | 11/2007 |
| WO | 2009135171 A2 | 11/2009 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

(56) References Cited

OTHER PUBLICATIONS

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp: 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, p. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N. a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

Extended European Search Report for corresponding Application No. 171939689, dated Jan. 16, 2018.

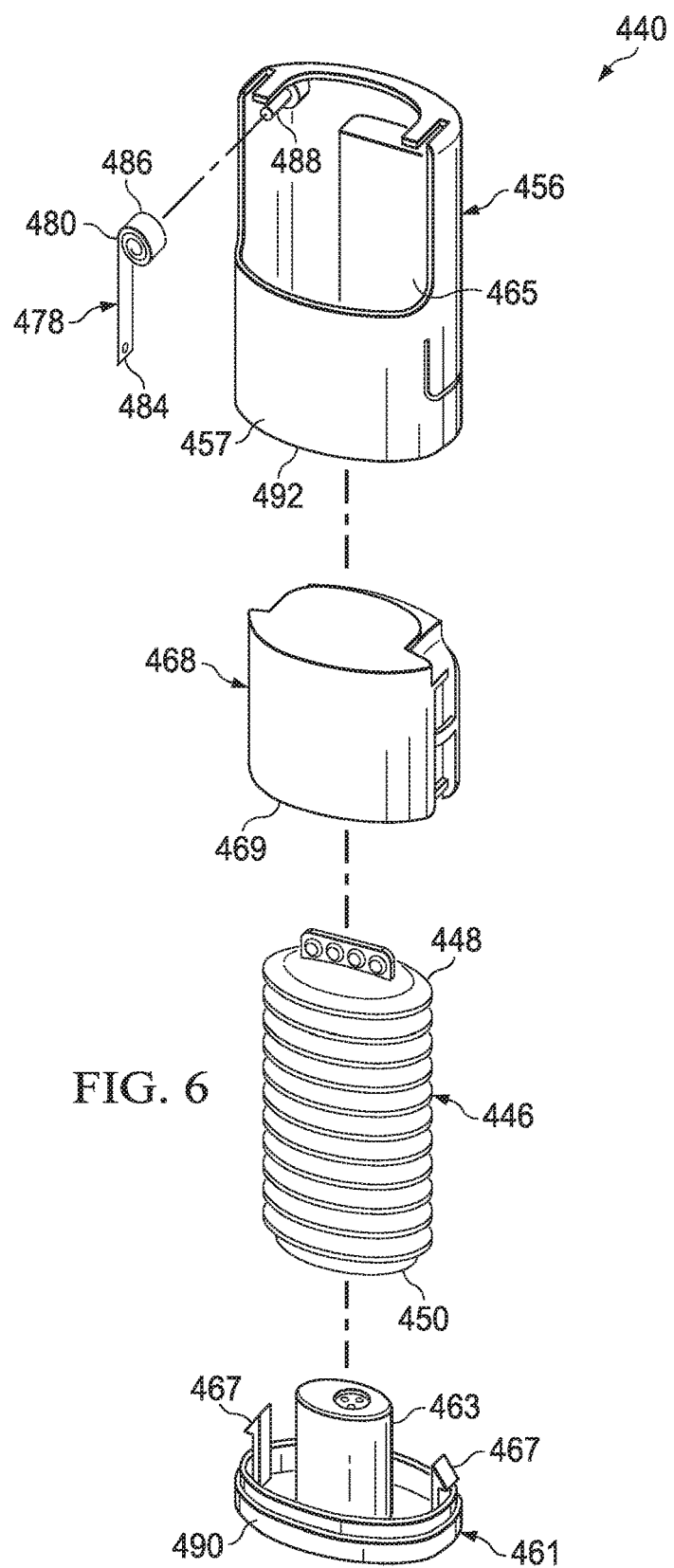

US 10,420,866 B2

MANUALLY-ACTUATED, REDUCED-PRESSURE SYSTEMS FOR TREATING WOUNDS

CROSS REFERENCE TO RELATED APPLICATIONS

This application is a continuation of U.S. patent application Ser. No. 14/145,723, filed Dec. 31, 2013, which is a divisional application of U.S. patent application Ser. No. 12/500,134, filed Jul. 9, 2009, now U.S. Pat. No. 8,641,692, which claims the benefit, under 35 U.S.C. § 119(e), of the filing of U.S. Provisional Patent Application No. 61/079,866, entitled "Manually-Actuated, Reduced-Pressure System for Treating a Wound," filed Jul. 11, 2008, which is incorporated herein by reference for all purposes.

BACKGROUND

The present invention relates generally to medical treatment systems and particularly to manually-actuated, reduced-pressure systems and apparatuses for treating wounds.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad may be incorporated into a dressing having other components that facilitate treatment.

Reduced-pressure treatment systems are often applied to large, highly exudating wounds present on patients undergoing acute or chronic care, as well as other severe wounds that are not readily susceptible to healing without application of reduced pressure. Low-severity wounds that are smaller in volume and produce less exudate have generally been treated with dressings and not with reduced pressure. The expense and need for trained caregivers to administer and maintain reduced-pressure systems have been a detriment to use. At the same time, size and power requirements have been a detriment to many patients who desire mobility and comfort. Further still, the expense of systems has made it difficult to justify use of reduced pressure on low-severity wounds.

One of the challenges of treating wounds with reduced pressure is providing an effective manner of producing a constant source of reduced pressure. Currently, battery-operated pumps are often used to provide a reduced pressure to the wound site. However, these pumps are costly and require maintenance to ensure the batteries do not run out of power while the wound therapy is occurring. The loss of battery power may result in a long period of time until the reduced pressure is restored to the site due to the time involved to change the battery or make other provisions. Moreover, if the reduced pressure at the site is not maintained properly, leaks can occur at the wound site limiting the effectiveness of the reduced-pressure therapy.

SUMMARY

Problems with existing reduced-pressure sources and systems are addressed by the systems, apparatus, and methods of the illustrative embodiments described herein. According to an illustrative embodiment, a manually-actuated, reduced-pressure system for treating a wound on a patient includes a manifold member, a sealing member, a reduced-pressure delivery member, a reduced-pressure interface, and a manually-actuated, constant reduced-pressure source for generating a reduced pressure. The manifold is operable to distribute a reduced pressure. The sealing member is operable to provide a fluid seal over the manifold member and a portion of the patient. The reduced-pressure delivery member transmits reduced pressure from the manually-actuated, constant reduced-pressure source to the reduced-pressure interface. The manually-actuated, constant reduced-pressure source includes a reduced-pressure port that is fluidly coupled to a first end of the reduced-pressure delivery member. The manually-actuated, constant reduced-pressure source includes a constant-force biasing member.

According to another illustrative embodiment, a manually-actuated, reduced-pressure apparatus for use with a reduced-pressure system for treating tissue includes a flexible, collapsible member having a first end, a second end, and an interior space. The flexible, collapsible member is operable to move between a compressed position and an extended position. The manually-actuated, reduced-pressure apparatus further includes an evacuation port coupled to the flexible, collapsible member and a reduced-pressure port coupled to the flexible, collapsible member. The manually-actuated, reduced-pressure apparatus has a carrier member coupled to the first end of the flexible, collapsible member and a slider member coupled to the second end of the flexible, collapsible member. The slider member is operable to slidably engage the carrier member and to move between the compressed position and the extended position. The manually-actuated, reduced-pressure apparatus further includes a constant-force biasing member associated with carrier member and slider member and that is operable to urge the slider member and carrier member away from each other between the compressed position and the extended position.

According to another illustrative embodiment, a method of manufacturing a manually-actuated, reduced-pressure apparatus includes the steps of forming a carrier member, forming a slider member, and providing a flexible, collapsible member having a first end, a second end, and an interior space. The slider member and carrier member are formed to slidably engage one another. The flexible, collapsible member is moveable between a compressed position and an extended position. The method of manufacturing further includes the steps of coupling the first end of the flexible, collapsible member to the carrier member, coupling the second end of the flexible, collapsible member to the slider member, and associating a constant-force biasing member with the carrier member and slider member. The constant-force biasing member is operable to urge the carrier member and slider member away from each other between the compressed position and extended position. The method of manufacturing further includes the steps of associating an evacuation port with the flexible, collapsible member for allowing fluid to exit the interior space of the flexible, collapsible member when being placed in the compressed position and associating a reduced-pressure port with the flexible, collapsible member for delivering reduced pressure from the flexible, collapsible member.

According to another illustrative embodiment, a method of treating a tissue site on a patient with reduced pressure includes the steps of deploying a manifold member proximate the tissue site, deploying a sealing member over the manifold member and a portion of the patient's epidermis to form a fluid seal, coupling a reduced-pressure interface on the sealing member for providing reduced pressure to the manifold member, and providing a reduced-pressure source, wherein the reduced-pressure source is a manually-actuated, constant reduced-pressure source. The manually-actuated, constant reduced-pressure source includes a reduced-pressure port. The reduced-pressure port is fluidly coupled to the first end of the reduced-pressure delivery member and is operable to develop a substantially constant reduced pressure. The manually-actuated, constant reduced-pressure source includes a constant-force biasing member. The method of treating further includes the steps of fluidly coupling the reduced-pressure source to the reduced-pressure interface and moving the reduced-pressure source to the compressed position.

Other features and advantages of the illustrative embodiments will become apparent with reference to the drawings and detailed description that follow.

BRIEF DESCRIPTION OF THE DRAWINGS

FIG. 6 is a schematic perspective view of another illustrative embodiment of a manually-actuated, reduced-pressure apparatus.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
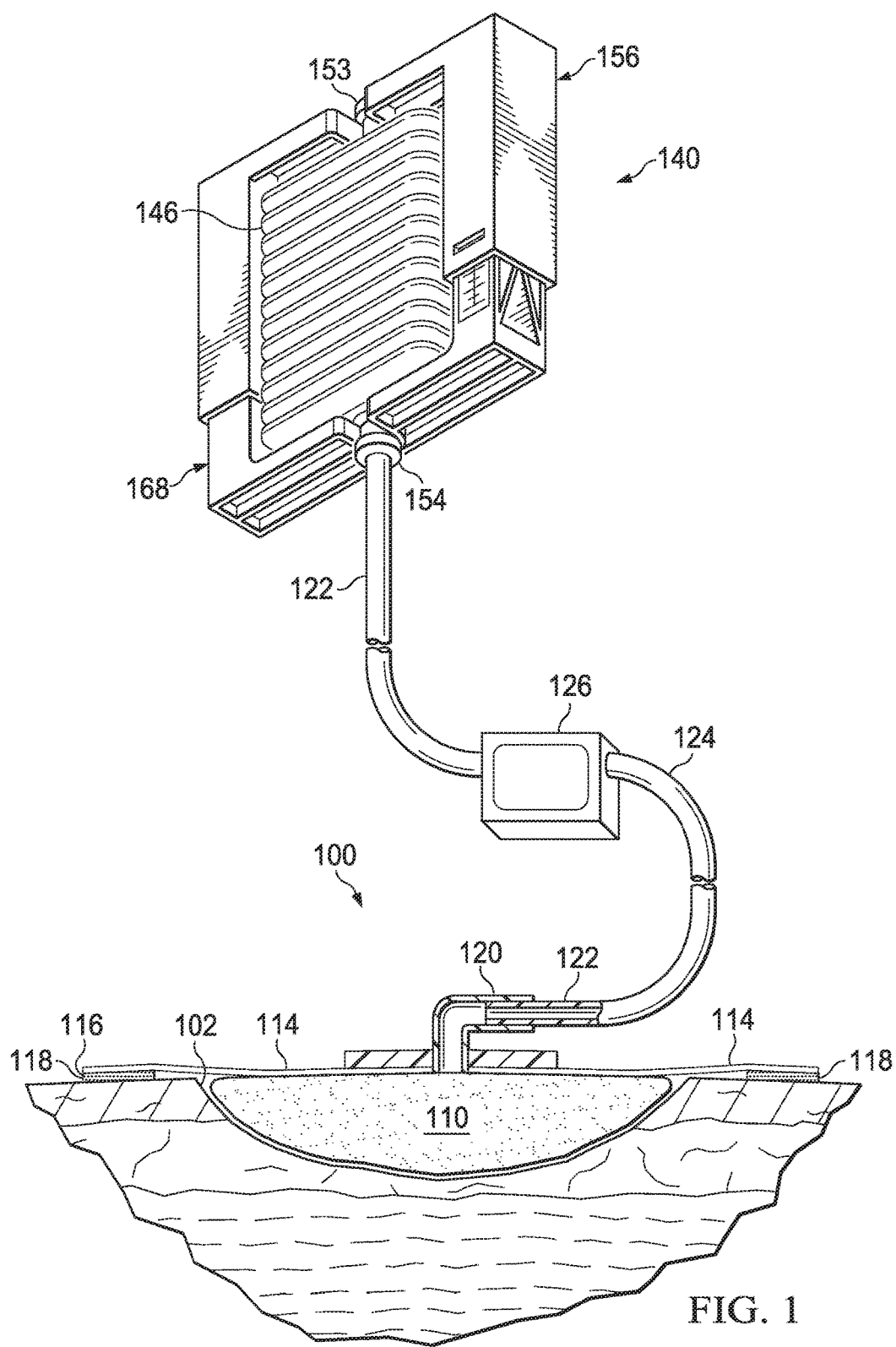
FIG. 1 is a schematic presentation of an illustrative embodiment of a manually-actuated, reduced-pressure system for treating a wound with a portion shown in cross-section and a portion shown in a perspective view.

Referring to FIG. 1, a manually-actuated, reduced-pressure system 100 for treating a tissue site 102 with a reduced pressure is shown. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue.

The reduced pressure may be applied to the tissue site 102 to help promote removal of exudates or other fluids from the tissue site or to stimulate the growth of additional tissue. Unless otherwise indicated, as used herein, "or" does not require mutual exclusivity. In the case of a wound at the tissue site 102, the growth of granulation tissue and removal of exudates and bacteria helps to promote healing of the wound. In the situation of a non-wounded or non-defective tissue, reduced pressure may be used to promote the growth of tissue that may be harvested and transplanted to another tissue site. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site 102. Unless otherwise indicated, values of pressure stated herein are gauge pressures. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The manually-actuated, reduced-pressure system 100 includes a manifold member 110, a sealing member 114, a reduced-pressure interface 120, and a reduced-pressure source 140, which is a manually-actuated, reduced-pressure apparatus. A reduced-pressure delivery member 122 fluidly couples the reduced-pressure source 140 to the reduced-pressure interface 120.

The manifold member 110 is placed at the tissue site 102. The manifold member 110 may be a biocompatible material that is capable of being placed in contact with the tissue site and distributing reduced pressure to the tissue site. The term "manifold" as used herein generally refers to a substance or structure that is provided to assist in applying reduced pressure to, delivering fluids to, or removing fluids from a tissue site. The manifold member 110 typically includes a plurality of flow channels or pathways that distribute fluids provided to and removed from the area of tissue around the manifold. The flow channels may be interconnected. Examples of manifolds may include, without limitation, devices that have structural elements arranged to form flow channels, cellular foam (such as open-cell foam), porous tissue collections, and liquids, gels and foams that include or cure to include flow channels. The manifold member 110 may be porous and may be made from foam, gauze, felted mat, or any other material suited to a particular biological application.

In one illustrative embodiment, the manifold member 110 is a porous foam and includes a plurality of interconnected cells or pores that act as flow channels. The porous foam may be a polyurethane, open-cell, reticulated foam, such as the GranuFoam® material manufactured by Kinetic Concepts, Incorporated of San Antonio, Tex. Other embodiments might include "closed cells." In some situations, the manifold may also be used to distribute fluids, such as medications, antibacterials, growth factors, and other solutions to the wound. Other layers may be included, such as absorptive materials, wicking materials, hydrophobic materials and hydrophilic materials.

The sealing member 114 is placed over the manifold member 110 and provides a fluid seal adequate for the manually-actuated, reduced-pressure system 100 to hold a reduced pressure at the tissue site 102. "Fluid seal," or "seal," means a seal adequate to hold reduced pressure at a desired site given the particular reduced-pressure subsystem or source involved. The sealing member 114 may be a cover that is used to secure the manifold member 110 at the tissue site 102. While the sealing member 114 may be impermeable or semi-permeable, the sealing member is capable of maintaining a reduced pressure at the tissue site 102 after installation of the sealing member 114 over the manifold member 110 and a portion of the patient's epidermis. The sealing member 114 may be a flexible over-drape or film formed from a silicone based compound, acrylic, polyurethane, hydrogel or hydrogel-forming material, or any other biocompatible material that includes the impermeability or permeability characteristics desired for the tissue site 102.

The sealing member 114 may further include an attachment device 116 to secure the sealing member 114 to a patient's skin. The attachment device 116 may take many forms. For example, an adhesive layer 118 may be positioned along a perimeter of the sealing member or any portion of the sealing member to provide the fluid seal. The adhesive layer 118 may also be pre-applied and covered with a release member that is removed at the time of application.

The reduced-pressure interface 120, or connector, permits the passage of fluid from the manifold member 110 to the reduced-pressure delivery member 122 and vice versa. For example, exudates collected from tissue site using the manifold member 110 may enter the reduced-pressure delivery member 122 via the reduced-pressure interface 120. In another embodiment, the system 100 may not include the reduced-pressure interface 120 and the reduced-pressure delivery member 122 may be inserted directly through the sealing member 114 and into the manifold member 110. The reduced-pressure delivery member 122 may be a medical conduit or tubing or any other device for enabling transportation or transmission of reduced pressure.

Reduced pressure is generated and supplied to the reduced-pressure delivery member 122 by the reduced-pressure source 140, which is a manually-actuated, reduced-pressure apparatus. The reduced-pressure source 140 may include a flexible, collapsible member 146 that is associated with a carrier member 156 and a slider member 168. As used herein, "associated" means to bring together or into relationship in any of various ways, such as permanently coupling one to another, releasably coupling one to another, aligning members to allow one member to push or pull another member, etc.

While not explicitly shown in FIG. 1, the reduced-pressure source 140 includes a constant-force biasing member that urges slider member 168 away from carrier member 156. The reduced-pressure source 140 has an evacuation port 153 that allows the air or other fluid in the flexible, collapsible member 146 to exit, but not enter the evacuation port 153. Reduced pressure is delivered by the reduced-pressure source 140 through a reduced-pressure port 154, which is coupled to the reduced-pressure delivery member 122 and may be operable to allow flow in only one direction—from the reduced-pressure delivery member 122 into the flexible, collapsible member 146. By using the constant-force biasing member, the reduced-pressure source 140 is operable to develop a constant reduced pressure. As used herein, "constant" means that a particular reduced pressure may be maintained at the reduced-pressure port 154 at a given level plus or minus five percent. The strength of the constant-force biasing member is a variable for establishing the reduced pressure level produced by the reduced-pressure source 140.

A number of different devices may be added to a medial portion 124 of the reduced-pressure delivery member 122. For example, a fluid collection member 126 may be added to hold exudates and other fluids removed (the fluids may also be held within the flexible, collapsible member 146). Other examples of devices that may be included on the medial portion 124 of the reduced-pressure delivery member 122 include a pressure feedback device, volume detection system, blood detection system, infection detection system, flow monitoring system, temperature monitoring system, etc. Some of these devices, e.g., the fluid collection member, may be formed integrally with the reduced-pressure source 140. The reduced-pressure port 154 may include a filter member that includes one or more filters and may include a hydrophobic filter that prevents liquid from entering an interior space within the collapsible member 146. An odor filter may also be included.

In operation, the manifold member 110 is deployed proximate the tissue site 102, and the sealing member 114 is deployed to create a fluid seal over the manifold member 110 and a portion of the patient's epidermis. If not already coupled, the reduced-pressure interface 120 is coupled to the sealing member 114. The reduced-pressure delivery member 122 is coupled between the reduced-pressure interface 120 and the reduced-pressure source 140. The slider member 168 is manually actuated or moved toward the carrier member 156 thereby collapsing the flexible, collapsible member 146 and placing the reduced-pressure source 140 in a compressed position. During this movement, air or other fluid in the interior space of the flexible, collapsible member 146 is forced out through the outlet evacuation port 153. Then, once released, as the biasing device urges the slider member 168 away from the carrier member 156, the biasing causes the flexible, collapsible member 146 to want to expand which generates a reduced pressure that is communicated through the reduced-pressure port 154 to the reduced-pressure delivery member 122 and on through the reduced-pressure interface 120 to the manifold member 110 and to the tissue site 102. As the delivery of reduced pressure causes gases or possibly other fluids to enter the reduced-pressure port 154, the flexible, collapsible member 146 expands and eventually fills to arrive at an expanded position. Depending on the circumstances, e.g., if the flexible, collapsible member 146 is not contaminated, the flexible, collapsible member 146 may be re-primed by placing the flexible, collapsible member 146 in the compressed position again and starting another cycle. An alarm may be added to audibly signal when the expanded position has been reached.

Figure 2:
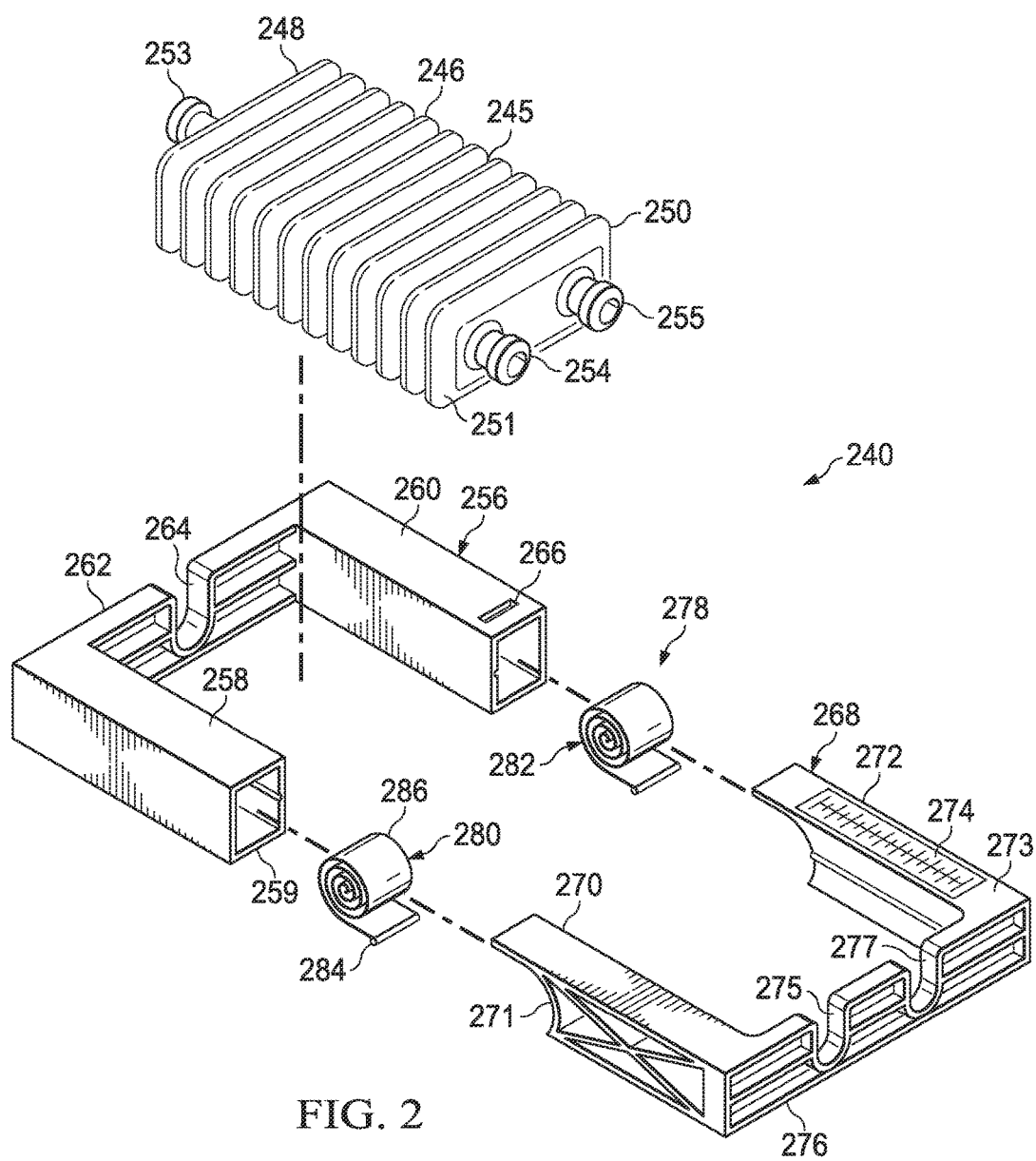
FIG. 2 is a schematic, exploded perspective view of an illustrative embodiment of a manually-actuated, reduced-pressure apparatus for use with a reduced-pressure system.

Referring now primarily to FIG. 2, a manually-actuated, reduced-pressure source 240 is shown in an exploded, perspective view. The manually-actuated, reduced-pressure source 240 includes a flexible, collapsible member 246 disposed between a carrier member 256 and a slider member 268. The carrier member 256 and the slider member 268 are urged away from each other by a constant-force biasing member 278.

The flexible, collapsible member 246 has a first end 248 and a second end 250. The flexible, collapsible member 246 may hold air or other fluid in an interior portion. An evacuation port 253 may be located near the first end 248 to allow the air or other fluid to exit the interior space of the flexible, collapsible member 246. A reduced-pressure port 254 may be located near the second end 250. During use, the reduced-pressure port 254 is fluidly coupled to a reduced-pressure delivery conduit, e.g., reduced-pressure delivery member 122 of FIG. 1, to provide reduced pressure to a system for treating tissue at a wound site. These ports 253, 254 may be located anywhere on the flexible, collapsible member 246.

In this illustrative embodiment, a nodule 255 is coupled to the flexible, collapsible member 246 near the second end 250. The nodule 255 is added for safety reasons. In particular, because the first end 248 has one evacuation port 253 and the second end 250 has reduced-pressure port 254 and nodule 255, the flexible, collapsible member 246 can only be mated with the carrier member 256 and the slider member 268 in one direction. Thus, the flexible, collapsible member 246 may only be installed in the correct way.

In one illustrative example, the flexible, collapsible member 246 may be formed as bellows. In such an illustrative embodiment, the flexible, collapsible member 246 is formed with corrugated side walls 245 with corrugations that may move toward and away from one another, resulting in a compression and expansion of compressible bellows. The flexible, collapsible member 246 may be made from any material, e.g., a flexible polymer, which allows for the compression and expansion of the bellows. The shape may be rectangular, circular, or any other shape. The flexible, collapsible member 246 may be coupled to the carrier member 256 and slider member 268 by being welded, screwed, glued, bolted, air-lock sealed, snapped or by any other means. The term "coupled" generally includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling.

The inner chamber of the flexible, collapsible member operates as a closed system such that the pressure and volume have a defined relationship, i.e., $P_1*V_1=P_2*V_2$. The area of an end wall 251 of the flexible, collapsible member 246 experiences pressure and transmits a force to the slider member 268. The force is proportional to the area ($F \approx PA$). The reduced pressure generated can be controlled by selecting the force of the constant-force biasing member 278 and controlling the area of the end wall 251. The pressure developed by the manually-actuated, reduced-pressure source 240 is generally inversely proportional to the area on the interior portion of the end wall 251 of the flexible, collapsible member 246 that faces a slider lateral slider member 276 ($P \approx F/A$).

The carrier member 256 is shown in this illustrative embodiment as having a first socket member 258 and a second socket member 260. As will be explained further below, the socket members 258 and 260 are sized to receive a first constant-force coil spring 280 and a second constant-force coil spring 282, respectively, and a first arm 270 and a second arm 272 of the slider member 268, respectively.

The first socket member 258 and second socket member 260 are coupled by a lateral carrier member 262. The lateral carrier member 262 is formed with a port channel 264. The port channel 264 is sized and configured to securely receive, such as by an interference fit, the evacuation port 253. The socket members 258 and 260 may be formed with an indicator window 266 through which a scale, markings, or other visual indicia 274 on an exterior surface 273 of the slider member 268 may be viewed. The carrier member 256 may be formed as a plurality of components that are coupled through welding, adhesives, bolting, snap fitting, screws, or by any other coupling or may be formed as an integral unit such as by casting. The two coil springs 280, 282 could be placed in a single socket member; in that case, it may be desirable to place the indicator window on the opposite side from the side with springs.

The slider member 268 is formed with a first arm 270 and a second arm 272 and has a lateral slider member 276 coupled between the arms 270, 272. The lateral slider member 276 has a first port channel 275 and a second port channel 277 that are sized and configured to securely receive, e.g. with an interference fit, the reduced-pressure port 254 and the nodule 255 (or simulated port), respectively. The visual indicia 274, such as a scale, may be placed on the exterior surface 273 of one of the arms, e.g., second arm 272.

In this illustrative embodiment, the constant-force biasing member 278 includes the first constant-force coil spring 280 and the second constant-force coil spring 282. The first constant-force coil spring 280 has a fixation portion 284 and a coil portion 286. The fixation portion 284 is coupled proximate to a socket opening 259 of the first socket member 258 and the socket opening 259 is sized to receive the coil portion 286 of the first constant-force coil spring 280. The first arm 270 of the slider member 268 is formed with an interface area 271, or member, that may be concave as shown, and is made to contact the coil portion 286 and to unroll the coil portion 286 or deflect the coil portion 286 as the slider member 268 is manually actuated towards the carrier member 256.

Figure 3A:
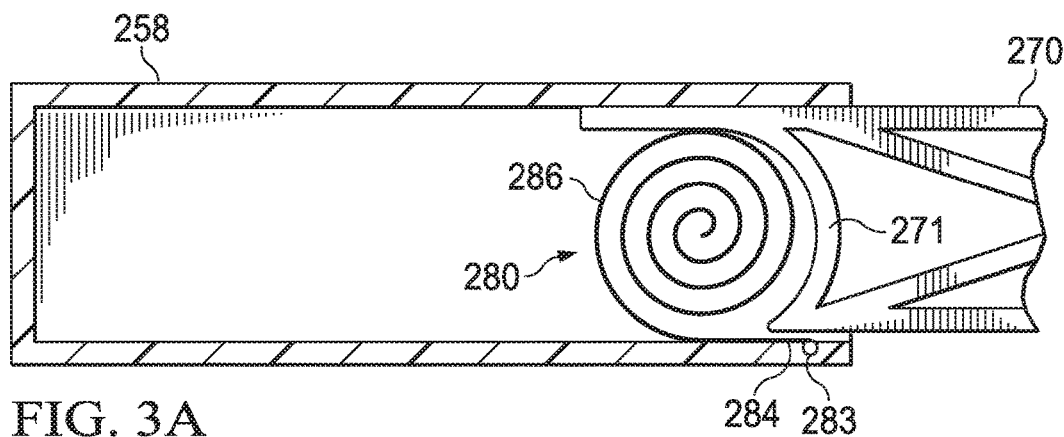
FIGS. 3A and 3B are schematic cross-sections of a portion of the apparatus of FIG. 2.
Figure 3B:
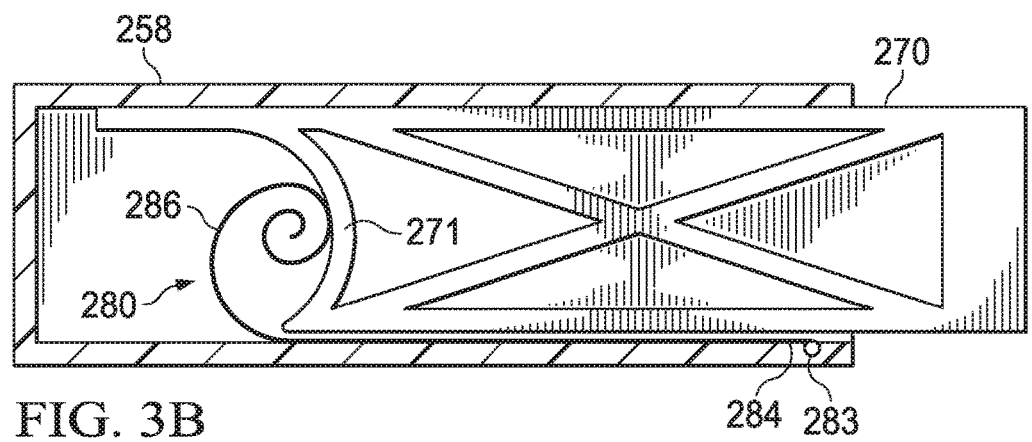

Referring now primarily to FIGS. 3A and 3B, a schematic cross-section of the first socket member 258, first constant-force coil spring 280, and first arm 270 are shown initially in an extended position in FIG. 3A, and then in a compressed position in FIG. 3B. Beginning in the extended position of FIG. 3A, the coil portion 286 is near its natural free position, or length. The fixation portion 284 of the first constant-force coil spring 280 is coupled using a coupling device 283, such as a spring retainer or a pin, etc. As the first arm 270 is urged into the first socket member 258, the interface area 271 presses against the coil portion 286 of the first constant-force coil spring 280 and causes the coil portion 286 to unroll at least partially and all the while the first constant-force coil spring 280 provides a constant force that resists the load being placed on the first constant-force coil spring 280.

As the first arm 270 is urged to the first arm's stopping spot as shown in FIG. 3B, and released, the first constant-force coil spring 280 will continue to urge the first arm 270 away from and out of the first socket member 258. Returning again to FIG. 2, it should be understood that the second constant-force coil spring 282 interacts with the second socket member 260 and the second arm 272 in a manner analogous to that shown in FIGS. 3A and 3B for the first constant-force coil spring 280.

Figure 4A:
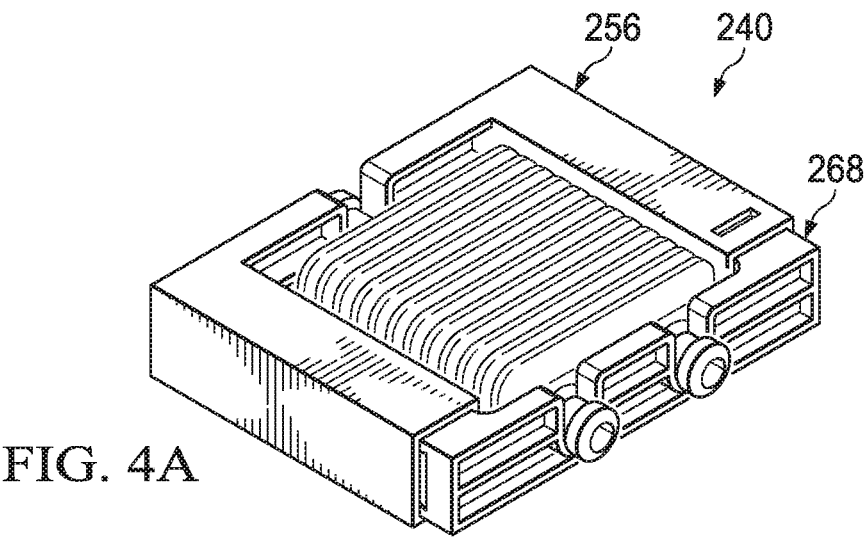
FIGS. 4A, 4B, and 4C present an illustrative embodiment of a manually-actuated, reduced-pressure apparatus shown in a compressed position, an intermediate position, and an expanded position, respectively.
Figure 4B:
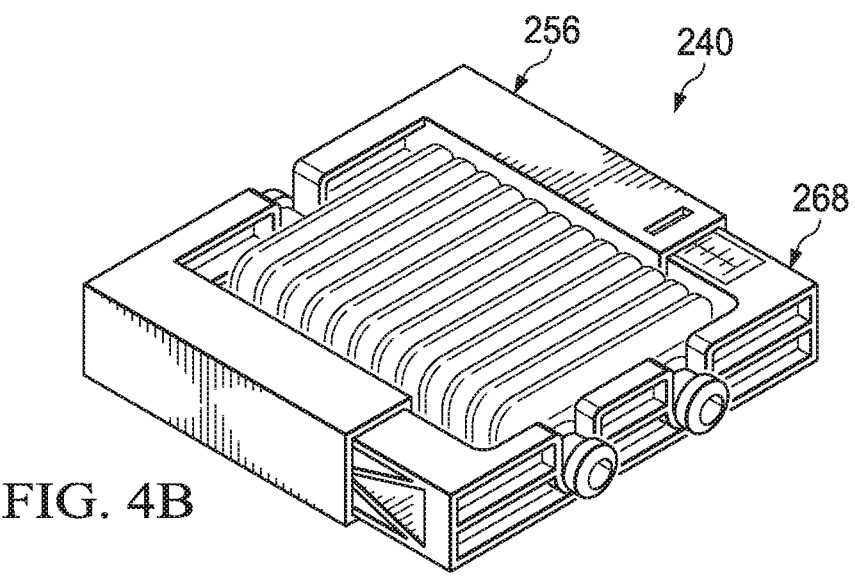
Figure 4C:
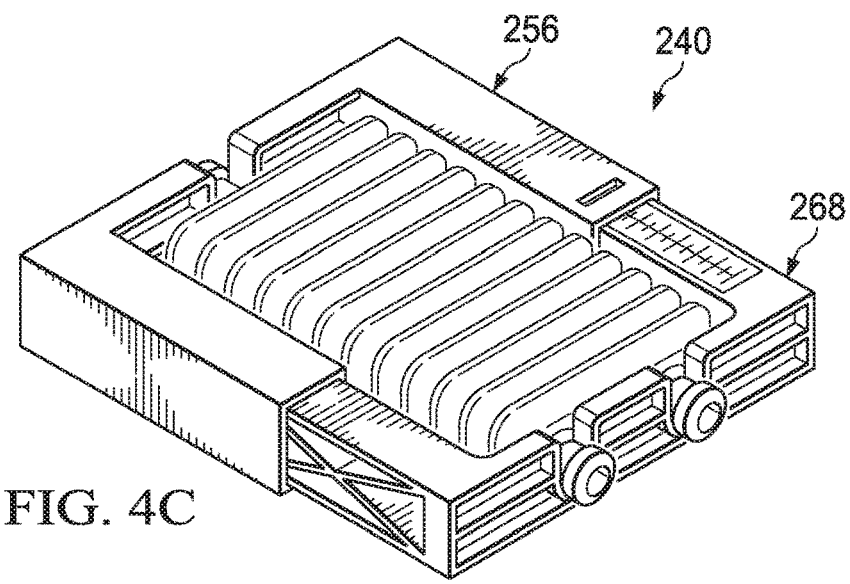

In operation, the manually-actuated, reduced-pressure source 240 generates a reduced pressure as the manually-actuated, reduced-pressure source 240 moves from a compressed position as shown in FIG. 4A to an intermediate position shown in FIG. 4B and ending in an extended position shown in FIG. 4C. To prepare the manually-actuated, reduced-pressure source 240 for use in a reduced-pressure treatment system, the flexible, collapsible member 246 is placed with the evacuation port 253 in the port channel 264 of the carrier member 256 and the reduced-pressure port 254 and the nodule 255 are placed in the first port channel 275 and the second port channel 277, respectively. A reduced-pressure delivery conduit may be connected to the reduced-pressure port 254. Then the slider member 268 is urged towards the carrier member 256 by manually pressing, or activating, the members together such as, for example, with one's hand. As this is done, the constant-force coil springs 280 and 282 unwind and the manually-actuated, reduced-pressure source 240 arrives at the compressed position (see FIGS. 3B and 4A).

Then the manual force that was applied is removed and the springs 280 and 282 urge the slider member 268 away from the carrier member 256. This urging starts to expand the flexible, collapsible member 246 and that places a suction on the reduced-pressure port 254. As gas or other fluid is received into the reduced-pressure port 254, the manually-actuated, reduced-pressure source 240 again reaches equilibrium as the slider member 268 is moved out from the carrier member at least to some degree. This process continues through the intermediate positions all the way until the manually-actuated, reduced-pressure source 240 reaches a final, or extended, position (see FIGS. 3A and 4C) where either the flexible, collapsible member 246 being completely full, or the springs 280, 282 having reached their beginning position.

Figure 5:
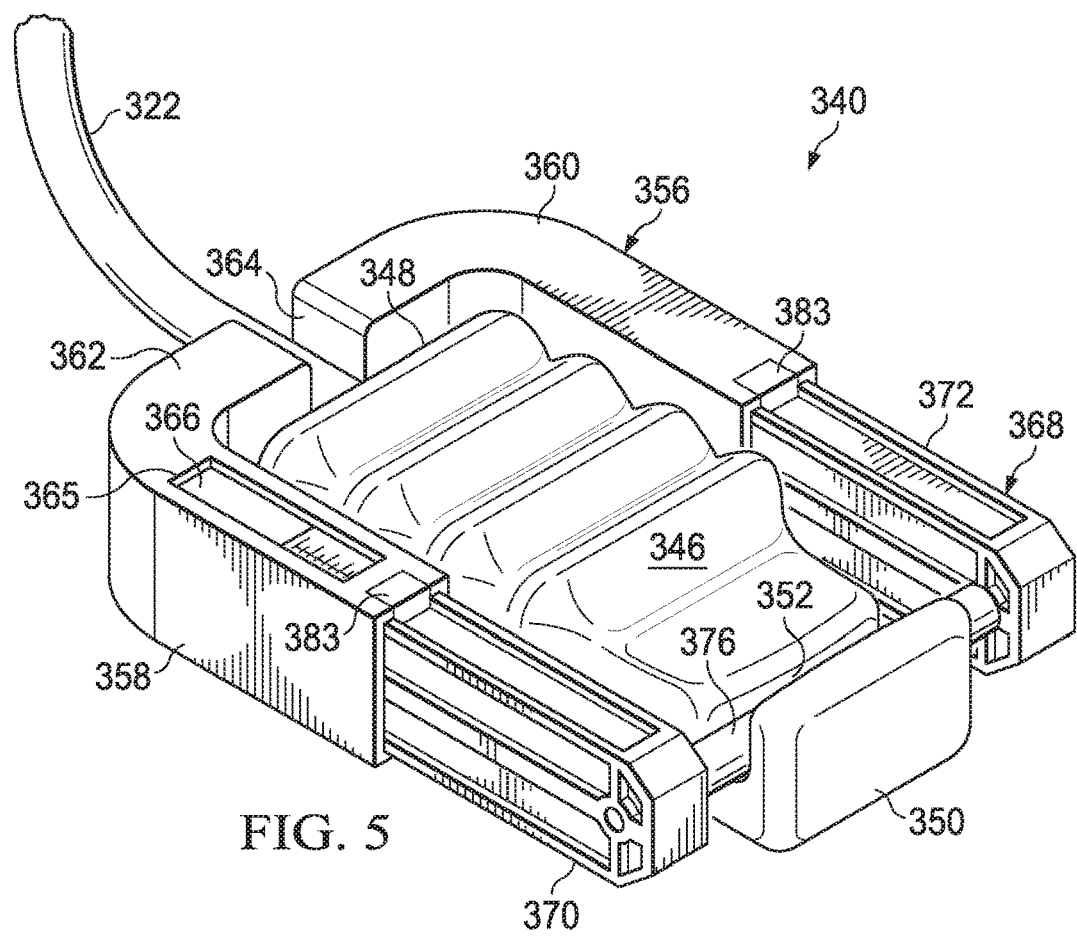
FIG. 5 is a schematic perspective view of another illustrative embodiment of a manually-actuated, reduced-pressure apparatus.

Referring now primarily to FIG. 5, another illustrative embodiment of a manually-actuated, constant reduced-pressure source 340 is presented. The manually-actuated, constant reduced-pressure source 340 includes a flexible, collapsible member 346, a carrier member 356, and a slider member 368. Retention members 383 couple a constant-force biasing member (not shown) within a portion of the carrier member 356. The constant-force biasing member provides a force that urges the slider member 368 away from the carrier member 356 as the manually-actuated, constant reduced-pressure source 340 moves from a compressed position to an extended position.

The carrier member 356 includes a first socket member 358, a second socket member 360, and a carrier lateral member 362. The carrier member 356 may be formed by component parts that are coupled or may be formed as an integral unit by such means as casting. An indicator 365 may be included as a part of the manually-actuated, constant reduced-pressure source 340 to indicate remaining capacity or movement. As one example, the indicator 365 may be an indicator window 366 formed on the first socket member 358 or the second socket member 360 that allows for visual indicia that is attached to a portion of the slider member 368 to be seen and thereby provides an indication of how much further the manually-actuated, constant reduced-pressure source 340 can move before reaching its fully-extended position. A port channel 364 may be formed on the carrier lateral member 362 to help hold a port, such as a reduced-pressure port through which the reduced pressure that is generated within the flexible, collapsible member 346 may be delivered to a reduced-pressure delivery conduit 322, which transmits the reduced pressure on to a system for treating tissue at a wound site.

The slider member 368 has a first arm 370 and a second arm 372. The arms 370, 372 are connected by a slider lateral member 376. The slider lateral member 376 may be snapped into position on the two arms 370, 372. In a manner analogous to that shown in FIGS. 3A and 3B, the arms 370, 372 may push a constant-force biasing member located within the socket members 358 and 360.

The flexible, collapsible member 346 has a first end 348 and a second end 350. A portion of the second end 350 may be formed intentionally to hold fluids, such as exudate that may gather within the interior space of the flexible, collapsible member 346. An absorption gel or other absorption material may be placed within an interior portion of the collapsible member, such as near the second end 350. The first end 348 of the flexible, collapsible member 346, in this particular illustrative embodiment, includes a reduced-pressure port that fits within the port channel 364 on the carrier member 356. The fit, e.g., an interference fit, may be tight enough to help hold the first end 348 securely to the carrier member 356 or other means of coupling the first end 348 may be utilized such as fasteners, welding, adhesives, etc. The second end 350 of flexible, collapsible member 346 is formed with a channel or groove or carrier lug 352 that is sized and configured to receive the slider lateral member 376 and to hold the slider lateral member 376 and thereby secure the second end 350 to the slider member 368.

Referring now primarily to FIG. 6, another illustrative embodiment of a manually-actuated, reduced-pressure apparatus 440 is presented in an exploded perspective view. The manually-actuated, reduced-pressure apparatus 440 includes a flexible, collapsible member 446, a carrier member 456, which includes a housing portion 457, or casing, and a base member 461. The manually-actuated, reduced-pressure apparatus 440 further includes a slider member 468 and a constant-force biasing member 478.

The flexible, collapsible member 446 has a first end 448 and a second end 450. In this embodiment, the first end 448 is coupled inside of a slider member 468 and the second end 450 is coupled to a base pod 463 of the base member 461.

The housing portion 457, or casing, of the carrier member 456 is made to snap into position with the base member 461 to form an integral unit, and this can be done with both a lip portion 490 and with detents, or detent arms 467, that engage the housing portion 457. The detent arms 467 may be used to engage and hold a portion of housing portion 457 and a lip portion 490 may be included to receive and hold the housing portion 457 proximate opening 492. The housing portion 457 may include a slider opening 465 in which the slider member 468 may be slidably coupled and may be manually depressed within the slider opening 465.

The base member 461 may include a reduced-pressure port (not shown) analogous to reduced-pressure port 254 of FIG. 2 for allowing a delivery conduit to be attached and to receive and transmit reduced pressure. The reduced-pressure port 254 is fluidly coupled to an interior space of the flexible, collapsible member 446. The reduced-pressure port 254 may include a counter-bore into the flexible, collapsible member 446 and preferably into a portion of flexible, collapsible member 446 for holding any fluids that might enter. The port may further include a filter carrier with a filter member; the filter member may include a charcoal pellet filter and a sintered hydrophobic filter.

The slider member 468 is formed with an opening 469. The slider member 468 is sized to be operable to slide within a portion of the housing portion 457.

The constant-force biasing member 478 may be a constant-force, coil spring 480 with a fixation portion 484 and a coil portion 486. The center opening of the coil portion 486 may be placed upon a drum or pin 488 located on the housing portion 457. The fixation portion 484 may be secured near the slider opening 469.

In the final assembly of the manually-actuated, reduced-pressure apparatus 440, the flexible, collapsible member 446 is coupled to the base pod 463 where the flexible collapsible member will be held secure and where the flexible, collapsible member 446 is placed into fluid contact with a reduced-pressure port. The first end 448 of the flexible, collapsible member 446 is placed within opening 469 of the slider member 468 and coupled to a portion of the slider member 468. The housing portion 457 is placed over the slider member 468 and the flexible, collapsible member 446 is depressed until the detent arms 467 engage a corresponding receptacle within the opening 492 of the housing portion 457 and the lip 490 engages the opening 492. The constant-force biasing member 478, for example, the constant-force, coil spring 480, is coupled to apparatus 440 by placing the center opening of the coil portion 486 onto the drum 488 of the carrier member 456 and coupling the fixation portion 484 near the opening 469 of the slider member 468.

In operation, a reduced-pressure delivery conduit is attached to a reduced-pressure port on the base member 461 and then slider member 468 may be depressed, or manually-actuated, by pushing the slider member 468 down further into slider opening 465 to cause manually-actuated, reduced-pressure apparatus 440 to assume a compressed position in which the flexible, collapsible member 446 is collapsed. As the flexible, collapsible member 446 collapses, the air or other fluid within the manually-actuated, reduced-pressure apparatus 440 is forced out of an evacuation port, which also may be on the bottom side of the base member 461 (analogous to evacuation port 253 of FIG. 2).

As the coil spring 480 urges the slider member 468 away from the base member 461 of the carrier member 456, a reduced pressure is developed within the interior space of the flexible, collapsible member 446. This reduced pressure is communicated to the reduced-pressure port. The constant reduced pressure is thus supplied until the flexible, collapsible member 446 is full of air or other fluid and fluids or until the resting place or free length of the constant-force, coil spring 480 is reached. The apparatus provides a constant reduced pressure with only small variation. Over a period of time the manually-actuated, reduced-pressure apparatus 440 is able to compensate for the ingress by gas or liquid within the flexible, collapsible member 446. The magnitude of the reduced pressure may be designed and controlled by varying an area of the end of the flexible, collapsible member 446 as well as the spring force of the constant-force, coil spring 480.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A manually-actuated, reduced-pressure apparatus for use with a reduced-pressure system for treating tissue at a tissue site, the apparatus comprising:
    a flexible, collapsible member having an interior space, a first end coupled to a slider member, and a second end coupled to a base member, wherein the flexible, collapsible member is operable to move between a compressed position and an extended position;
    a constant-force biasing member operable to provide a constant force through a range of motion of the constant-force biasing member;
    a carrier member coupled to the base member and housing the flexible, collapsible member and the constant-force biasing member, the carrier member including a slider member opening, wherein at least a portion of the slider member is configured to extend out of the carrier member through the slider member opening;
    an evacuation port coupled to the flexible, collapsible member; and
    a reduced-pressure port fluidly coupled to the interior space of the flexible, collapsible member.

2. The manually-actuated, reduced-pressure apparatus of claim 1, wherein the constant-force biasing member is configured to transition from an unrolled state to a rolled state, urge at least a portion of the slider member out of the carrier member, and urge the flexible, collapsible member from the compressed position to the extended position.

3. The manually-actuated, reduced-pressure apparatus of claim 1, wherein the constant-force biasing member comprises a constant-force coil spring.

4. The manually-actuated, reduced-pressure apparatus of claim 1, wherein the constant-force biasing member comprises a constant-force coil spring coupled to the carrier member, the constant-force coil spring operable to provide a constant force urging the slider member from the compressed position to the extended position.

5. The manually-actuated, reduced-pressure apparatus of claim 1, wherein the constant-force biasing member comprises a first constant-force coil spring and a second constant-force coil spring coupled to the carrier member and operable to provide a constant force urging the slider member from the compressed position to the extended position.

6. The manually-actuated, reduced-pressure apparatus of claim 1, further comprising an indicator coupled to the carrier member for indicating movement of the flexible, collapsible member between the compressed position and the extended position.

7. The manually-actuated, reduced-pressure apparatus of claim 1, wherein the carrier member is formed with an indicator window and further comprising visual indicia secured on the slider member, and wherein a portion of the visual indicia is configured to be seen through the indicator window.

8. The manually-actuated, reduced-pressure apparatus of claim 1, wherein the flexible, collapsible member comprises a bellows.

9. A method of manufacturing a manually-actuated, reduced-pressure apparatus, the method comprising the steps of:
    providing a carrier member including a slider member opening;
    inserting a flexible, collapsible member into the carrier member, wherein the flexible, collapsible member has a first end, a second end, and an interior space and is moveable between a compressed position and an extended position;
    inserting a constant-force biasing member into the carrier member, wherein the constant-force biasing member is operable to provide a constant force through a range of motion of the constant-force biasing member;
    inserting a slider member into the carrier member, wherein at least a portion of the slider member is configured to extend out of the carrier member through the slider member opening;
    coupling the first end of the flexible, collapsible member to a base member;
    coupling the base member to the carrier member;
    coupling the second end of the flexible, collapsible member to the slider member;
    forming an evacuation port on the flexible, collapsible member for allowing fluid to exit the interior space of the flexible, collapsible member when being placed in the compressed position; and forming a reduced-pressure port on the flexible, collapsible member for delivering a reduced pressure from the flexible, collapsible member.

10. The method of manufacturing a manually-actuated, reduced-pressure apparatus of claim 9, wherein the constant-force biasing member is configured to transition from an unrolled state to a rolled state, urge at least a portion of the slider member out of the carrier member, and urge the flexible, collapsible member from the compressed position to the extended position.

11. The method of manufacturing a manually-actuated, reduced-pressure apparatus of claim 9, wherein the constant-force biasing member comprises a constant-force, coil spring.

12. The method of manufacturing a manually-actuated, reduced-pressure apparatus of claim 9, wherein the constant-force biasing member comprises a constant-force spring, the method further comprising coupling a fixation portion of the constant-force spring to the carrier member and configuring the slider member to press against a coil portion of the constant-force spring.

13. The method of manufacturing a manually-actuated, reduced-pressure apparatus of claim 9, wherein the second end of the flexible, collapsible member has an area (A); wherein the area (A) and a force (F) provided by the constant-force biasing member are selected to produce a desired reduced pressure (RP) at the reduced-pressure port; and wherein RP~F/A.

14. The method of manufacturing a manually-actuated, reduced-pressure apparatus of claim 9, further comprising the step of coupling an indicator to the carrier member.

15. The method of manufacturing a manually-actuated, reduced-pressure apparatus of claim 9, further comprising the steps of:

attaching visual indicia to a portion of the slider member; and forming an indicator window on the carrier member configured to permit viewing of a portion of the visual indicia.

16. A method of treating a tissue site on a patient with reduced pressure, the method comprising the steps of:

deploying a manifold member proximate the tissue site;

deploying a sealing member over the manifold member and a portion of an epidermis to form a fluid seal;

coupling a reduced-pressure interface on the sealing member for providing reduced pressure to the manifold member;

providing a reduced-pressure source, wherein the reduced-pressure source comprises a manually-actuated, constant reduced-pressure source for generating a reduced-pressure, wherein the manually-actuated, constant reduced-pressure source has a reduced-pressure port, wherein the reduced-pressure port is fluidly coupled to a first end of a reduced-pressure delivery member and is operable to develop a substantially constant reduced-pressure, wherein a carrier member houses the manually-actuated, constant reduced-pressure source, a slider member, and a constant-force biasing member, the carrier member including a slider member opening, wherein the constant-force biasing member is configured to provide a constant force through a range of motion of the constant-force biasing member, and wherein the constant-force biasing member is configured to urge at least a portion of the slider member out of the carrier member through the slider member opening;

fluidly coupling the reduced-pressure source to the reduced-pressure interface; and moving the manually-actuated, constant reduced-pressure source to a compressed position to charge the constant-force biasing member.

17. The method of claim 16, wherein the constant-force biasing member is configured to provide a constant force through a range of motion of the constant-force biasing member by transitioning from an unrolled state to a rolled state.

18. The method of claim 16, wherein the constant-force biasing member is configured to urge the manually-actuated, constant reduced-pressure source from the compressed position to an extended position.

19. The method of claim 16, wherein the manually-actuated, constant reduced-pressure source comprises:

a flexible, collapsible member having a first end, a second end, and an interior space;

an evacuation port coupled to the flexible, collapsible member; and a reduced-pressure port coupled to the flexible, collapsible member.

* * * * *